(12) United States Patent
Glauser et al.

(10) Patent No.: US 11,964,273 B2
(45) Date of Patent: Apr. 23, 2024

(54) SEALABLE MICROFLUIDIC CHIP FOR THERMOCYCLING

(71) Applicant: Roche Molecular Systems, Inc., Pleasanton, CA (US)

(72) Inventors: Michael Glauser, Rotkreuz (CH); Daniel Müller, Rotkreuz (CH); Michael Zeder, Rotkreuz (CH); Uta Schaffner, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/888,923

(22) Filed: Feb. 5, 2018

(65) Prior Publication Data
US 2018/0221875 A1 Aug. 9, 2018

(30) Foreign Application Priority Data
Feb. 6, 2017 (EP) .................................. 17154811

(51) Int. Cl.
*C12Q 1/68* (2018.01)
*B01L 3/00* (2006.01)
(Continued)

(52) U.S. Cl.
CPC ...... *B01L 3/502715* (2013.01); *C12Q 1/6806* (2013.01); *B01L 3/50851* (2013.01); *B01L 7/52* (2013.01); *B01L 2200/027* (2013.01); *B01L 2200/0605* (2013.01); *B01L 2200/0642* (2013.01); *B01L 2200/0673* (2013.01); *B01L 2200/0684* (2013.01); *B01L 2200/0689* (2013.01); *B01L 2300/042* (2013.01); *B01L 2300/048* (2013.01); *B01L 2300/0816* (2013.01); *B01L 2300/0864* (2013.01); *B01L 2300/1805* (2013.01); *B01L 2400/0406* (2013.01); *B01L 2400/0487* (2013.01); *B01L 2400/0677* (2013.01)

(58) Field of Classification Search
None
See application file for complete search history.

(56) References Cited

U.S. PATENT DOCUMENTS

| | | | |
|---|---|---|---|
| 5,576,197 | A | 11/1996 | Arnold |
| 6,143,496 | A | 11/2000 | Brown et al. |

(Continued)

FOREIGN PATENT DOCUMENTS

| | | |
|---|---|---|
| WO | WO9847003 | 10/1998 |
| WO | 03035909 A2 | 5/2003 |

OTHER PUBLICATIONS

Abi-Samra, et al. (Lab on Chip, 2011, vol. 11, p. 723-726) (Year: 2011).*

(Continued)

*Primary Examiner* — Stephanie K Mummert
(74) *Attorney, Agent, or Firm* — Maneesh Gupta

(57) ABSTRACT

The present disclosure relates to reversible sealing of a microfluidic chip used for thermal incubation of an aqueous sample suspected to contain a target nucleic acid. The microfluidic chip contains a flow channel and a plurality of reaction compartments, into which the sample and a displacement fluid are introduced through an inlet port sealable by means of a sealing agent having a melting point above room temperature.

7 Claims, 4 Drawing Sheets

(51) Int. Cl.
*C12Q 1/6806* (2018.01)
*B01L 7/00* (2006.01)

(56) References Cited

U.S. PATENT DOCUMENTS

| | | | |
|---|---|---|---|
| 7,989,214 B2 * | 8/2011 | Bianchessi | B01L 3/50853 |
| | | | 436/174 |
| 2003/0138819 A1 * | 7/2003 | Gong | B01L 3/5027 |
| | | | 435/6.12 |
| 2010/0086990 A1 * | 4/2010 | Stanley | G01N 21/07 |
| | | | 435/286.1 |
| 2011/0003699 A1 * | 1/2011 | Yoder | B01L 7/52 |
| | | | 506/7 |
| 2015/0093815 A1 | 4/2015 | Kiani et al. | |
| 2016/0251701 A1 | 9/2016 | Chiou et al. | |

OTHER PUBLICATIONS

Qui et al. (Lab Chip, 2010, vol. 10, p. 3170-3177) (Year: 2010).*
Abi-Samra, et al. (Lab on Chip, 2011, 11, 723-726) (Year: 2011).*

* cited by examiner

SEALABLE MICROFLUIDIC CHIP FOR THERMOCYCLING

CROSS-REFERENCE TO RELATED APPLICATIONS

The present application claims the benefit of priority under 35 U.S.C. § 119(a) of EP17154811.8, filed Feb. 6, 2017. Reference is also made to EP16183569.9, filed Aug. 10, 2016; EP16002058.2 and EP16002057.4, each filed Sep. 23, 2016; EP16191425.4, filed Sep. 29, 2016; and EP16191811.5, EP16191771.1, EP16400044.0, each filed September 30. The disclosures of each of these applications are incorporated herein by reference in their entireties.

FIELD OF DISCLOSURE

The present disclosure belongs to the field of analytical systems for conducting biological or biochemical assays. Within this field, it relates to reversible sealing of a microfluidic chip used for thermal incubation of an aqueous sample suspected to contain a target nucleic acid.

BACKGROUND

Thermal incubation has become a prerequisite for numerous analytical processes in both basic research and clinical diagnostics. Methods such as Polymerase Chain Reaction (PCR) rely on precisely defined series (often referred to as thermocycling) of heating steps, or heating and cooling steps, in order to subject a fluid sample to thermal conditions in which specific parts of the reaction are induced. For instance, mostly quantitative denaturation of the individual strands of double-stranded template DNA (dsDNA) typically requires temperatures of more than 90° C., while annealing of the corresponding oligonucleotides often takes place at considerably lower temperatures between about 50 and 65° C.

Such reactions may be carried out in single tubes, in pluralities of such individual tubes, or in integrated arrangements such as multiwell plates. The latter often allow for enhanced throughput and easier workflows, as a given sample may be distributed to a considerable number of reaction compartments in a single working step.

Such plates may be arranged in the form of microfluidic chips, in which an internal flow channel is used for the distribution of a fluid sample to a plurality of reaction compartments, for instance microwells, integrated into an inner wall of the flow channel.

Effectively sealing such microfluidic chips, both with respect to the individual reaction compartments and to the flow channels, can be challenging depending on the type of sample and/or application. Various methods exist, such as physical covers, lids, caps, bonded/glued foils or membranes, or liquid seals like PDMS or glues.

One approach is provided by U.S. Pat. No. 6,143,496 which discloses addition of a displacement fluid such as oil to the flow channel, thereby removing the aqueous sample therefrom and covering the sample chambers lying underneath.

SUMMARY

In a first aspect described herein, a method is described for thermally incubating an aqueous sample suspected to contain a target nucleic acid. In brief, a microfluidic chip with an internal flow channel having multiple reaction compartments is provided. The aqueous sample is introduced through an inlet port into the flow channel and ultimately into the reaction compartments, after which step a displacement fluid is added to remove excess aqueous sample from the flow channel, thereby fluidically separating the newly created sample partitions within the reaction compartments from each other. A sealing agent with a melting point above room temperature is then applied in liquid form to the inlet port where it is allowed to solidify below its melting temperature such as to seal the port.

The thus prepared microfluidic chip is then transferred to a thermal incubation station and subjected to a series of heating steps, wherein the sealing agent is molten again and thereby allows for gas exchange and pressure equilibration between the inside and outside of the microfluidic chip. In a specific embodiment, the aqueous sample has a higher density than the sealing agent.

Another aspect disclosed herein is a microfluidic chip with an internal flow channel having multiple reaction compartments. The chip further has an inlet port connected to the flow channel, wherein the inlet port has a sealing agent with a melting point above room temperature attached to an inner wall in solid form. It is arranged so as to not obstruct liquid flow through the inlet port unless it is molten and then re-solidified in order to cover the inlet port.

Further described herein are a kit and an analytical system using the microfluidic chip.

Accordingly, provided herein is a method for thermally incubating an aqueous sample comprising a target nucleic acid, the method comprising the steps of: providing a microfluidic chip comprising a flow channel positioned between an upper plate and a lower plate, the flow channel being in fluid communication with an inlet port and a plurality of reaction compartments positioned on one or more surfaces of an inside wall of the upper plate and the lower plate; injecting the aqueous sample into the flow channel of the microfluidic chip through the inlet port, thereby dispensing the aqueous sample into the plurality of reaction compartments; injecting a displacement fluid into the flow channel of the microfluidic chip through the inlet port, thereby displacing the aqueous sample from the flow channel and fluidly separating one or more aqueous sample partitions within the plurality of reaction compartments from each other; applying to the inlet port a liquid sealing agent having a melting point above room temperature and subsequently allowing the sealing agent to solidify at a temperature below the melting point to seal the inlet port; transferring the microfluidic chip formed in step (d) containing the one or more aqueous sample partitions within the reaction compartments to a thermal incubation station; and subjecting the microfluidic chip to a series of heating steps, wherein in one or more heating steps, the melting temperature of the sealing agent is exceeded such that the sealing agent is molten, thereby allowing for an exchange of gas and pressure equilibration through the inlet port; wherein the aqueous sample, the displacement fluid, and the sealing agent are immiscible with each other, and the sealing agent has a lower density than the aqueous sample.

Also provided is a microfluidic chip for thermally incubating an aqueous sample comprising target nucleic acid, the microfluidic chip comprising, from a proximate to a distal end: an inlet port comprising an inner wall including a sealing agent positioned therein, said sealing agent having a melting point above room temperature and being immiscible with and having a lower density than the aqueous sample; and a flow channel positioned between an upper plate and a lower plate of the microfluidic chip, the flow channel being in fluid communication with the inlet port and a plurality of reaction compartments positioned on one or more surfaces of an inside wall of the upper plate and the lower plate.

A further embodiment of the disclosure is a kit for thermally incubating an aqueous sample suspected to contain a target nucleic acid, the kit comprising the microfluidic chip as described herein and a displacement fluid immiscible with both the aqueous sample and the sealing agent.

BRIEF DESCRIPTION OF THE FIGURES

FIG. 2A shows the chip having aqueous sample before the displacement fluid is introduced. FIG. 2B shows the introduction of the displacement fluid, and FIG. 2C shows the incorporation of the displacement fluid in the flow channel and the partitioning of the aqueous sample into compartments within the chip, thereby sequestering the sample in the compartments.

In FIG. 3A, the inlet port (6) has two portions of sealing agent (30) in solid state attached to its inner wall to the left and to the right, leaving a gap in between so as to not obstruct fluid passage of aqueous sample (10) or displacement fluid (20). In FIG. 3B, the sealing agent (30) in solid state is held by a reservoir in the shape of a groove (31) formed by an elongate semicircular depression of a portion of the inner wall of the inlet port (6). In FIG. 3C, the inlet port (6) is not pre-loaded with sealing agent (30) in solid state, but the latter is dispensed into the inlet port (6) in molten form by a pipetting needle (32). As shown in FIG. 3D, regardless of the method used to introduce sealing agent (FIGS. 3A-3C), the chip is subsequently heated to a temperature above the melting temperature of the sealing agent (30), such that the latter is molten and may flow into place to form an immiscible layer upon the surface of the displacement fluid (20) within the inlet port (6).

DETAILED DESCRIPTION

Figure 1:
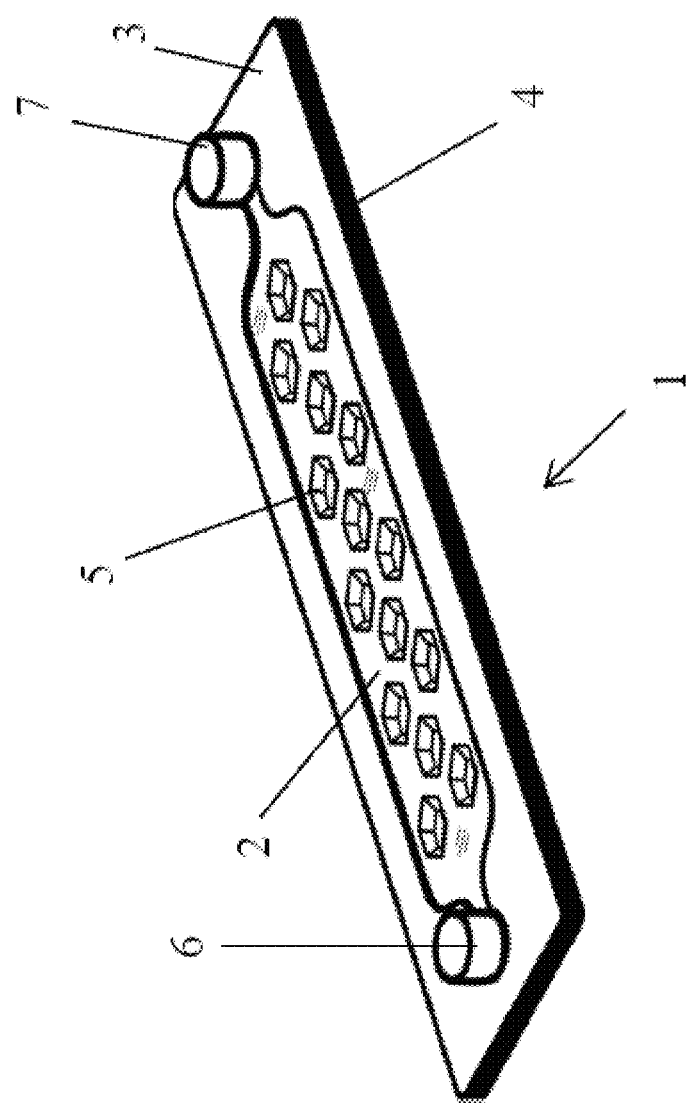
FIG. 1 shows a perspective view of the microfluidic chip (1) described herein.

A first aspect described herein is a method for thermally incubating an aqueous sample suspected to contain a target nucleic acid, the method comprising the steps of:
a. providing a microfluidic chip comprising a flow channel between an upper plate and a lower plate, the flow channel being in fluid connection with a plurality of reaction compartments on the inside wall of the upper plate and/or the lower plate;
b. injecting the aqueous sample into the flow channel of the microfluidic chip through an inlet port and thereby dispensing the aqueous sample into the plurality of reaction compartments;
c. injecting a displacement fluid into the flow channel of the microfluidic chip through an inlet port and thereby displacing the aqueous sample from the flow channel, thus fluidly separating the aqueous sample partitions within the individual reaction compartments from each other;
d. applying a sealing agent with a melting point above room temperature to the inlet port of the microfluidic chip and subsequently allowing it to solidify at a temperature below its melting point so as to seal the inlet port;
e. transferring the sealed microfluidic chip containing the aqueous sample partitions within the reaction compartments to a thermal incubation station;
f. subjecting the microfluidic chip to a series of heating steps, wherein in one or more steps the melting temperature of the sealing agent is exceeded such that it is molten, thereby allowing for the exchange of gas and pressure equilibration through the inlet port;
wherein the aqueous sample, the displacement fluid, and the sealing agent are immiscible with each other, and the sealing agent has a lower density than the aqueous sample.

The method described herein confers a number of advantages over the approaches used previously in the art. For instance, the sealing agent provides a means for spill protection with respect to the inlet port, since a device such as the microfluidic chip often needs to be transferred between individual units of an analytical system. The displacement fluid as such is usually not sufficient in order to avoid the loss of fluid—including the aqueous sample—in case the chip is moved, tilted, dropped, or the like. Similarly, since the displacement fluid is a liquid, the entry of contaminants through the inlet port and ultimately into the sample partitions in the reaction compartments is usually not substantially prevented by virtue of the displacement fluid alone.

One disadvantage of physical seals like caps or foils is that they are additional disposable components that have to be manufactured and handled separately which increases the cost and complexity of the workflow, and the cost of the disposable.

Chemical sealing solutions also require complex sealing hardware, such as dispenser, syringes, UV radiation etc. Moreover, short shelf-life of glues is a problem. Also highly reactive chemicals tend to clog tubing, valves, nozzles etc. which also requires more complex instrument design, or additional manual work. Further, many liquid glues display a higher density than aqueous solutions and thus tend to sink to the bottom of the inlet port that is filled with aqueous sample, which is not desired in some cases.

The sealing agent used in the presently described method, on the other hand, does not represent a separate disposable component, require complex sealing hardware, or cause a risk of chemically interfering with the sample to be analyzed, as its key feature for reversibly sealing the inlet port is its melting point above room temperature. Involving only elevated temperature instead of, for instance, radical starters, UV light, or the like, the sealing agent may be molten and applied through the inlet port onto the surface of the displacement fluid covering the aqueous sample partitions within the reaction compartments. Once the sealing agent has formed a continuous layer floating upon displacement fluid and/or aqueous sample, either in the inlet port or also within the flow channel, the temperature may be lowered to a value below the melting temperature of the sealing agent. In consequence, the molten sealing agent re-solidifies and thereby seals the inlet port and thus the microfluidic chip which, in some embodiments, does not have a further opening in addition to the inlet port. In some embodiments, the method described herein may generally be conducted at room temperature, such as between 20° C. and 30° C., or about 25° C. Melting of the sealing agent during or prior to step d. may be accomplished by heating elements, for instance, hot air, Peltier elements, or the like. The subsequently lowered temperature at which the sealing agent re-solidifies may be brought about by active cooling by cooling elements, for example, ventilation with cool air, or the like. In other embodiments, no active cooling is applied, but incubation at ambient temperature is sufficient. Since the displacement fluid is usually cooler than the molten sealing agent, the thermal exchange between molten sealing agent and displacement fluid may contribute to or even trigger re-solidification of the sealing agent.

Suitable sealing agents are substantially chemically inert so as not to react with either the displacement fluid or components of the aqueous sample. The melting temperature, also referred to as clearing temperature, is in some embodiments between about 25° C. and about 90° C., or between about 35° C. and about 80° C., or between about 45° C. and about 75° C. In some embodiments, the sealing agent has a melting temperature of about 55 to 71° C. In some embodiments the sealing agent is a wax such as paraffin wax. Wax, in particular, features a number of beneficial properties, like defined melting points, fast melting and solidifying, low density, low cost, low toxicity, low reactivity, chemical inertness, low auto fluorescence, good biocompatibility, and more.

For instance, U.S. Pat. No. 6,143,496 teaches a displacement fluid being a curable adhesive which is hardened after filling it into the flow-through channel. Such cured compounds like, for instance, an epoxy resin, do provide spill protection, but at the same time prevent gas exchange and/or pressure equilibration through the inlet port. Especially where the inlet port is the only opening through which the flow channel communicates with the surroundings of the chip, this may lead to problems within the reaction compartments. For example, the elevated temperatures typically applied during a PCR may lead to the formation and/or expansion of air bubbles within the reaction compartments. Such bubbles often interfere with detection methods such as fluorescence measurements, or even lead to displacement of the sample partition from one reaction compartment to a neighboring one. A so obtained analytical or even diagnostic result will not be treated as valid, such that the experiment must be repeated and the assayed sample is lost. This is of particular concern in the case of clinical samples, as it is in many cases complicated or even impossible to obtain further equivalent samples in order to conduct further diagnostic tests. Moreover, it often correlates with an additional strain put on the affected patient.

The use of a sealing agent with a melting point above room temperature in the presently described method solves these problems by being molten in the course of one or more steps of the thermal incubation. Its low density ensures that it remains floating upon the aqueous sample and in some embodiments also upon the displacement fluid even in liquid state, yet at the same time permits the exchange of gas and pressure equilibration through the inlet port.

As a consequence, the solidified sealing agent efficiently reduces the risk of contamination and spilling through the inlet port after filling of the microfluidic chip, and additionally ensures a thermal incubation of the aqueous sample partitions in the chip which is not jeopardized by obstructed gas exchange or lack of pressure equilibration.

In some embodiments of the method described herein, the order of density from high to low is aqueous sample>displacement fluid>sealing agent. In these embodiments, the molten sealing agent floats on top of the displacement fluid which in turn floats on top of the aqueous sample.

An "aqueous sample" is any fluid material on a water basis that can be subjected to a diagnostic assay and is in some embodiments derived from a biological source. An aqueous sample can be pipetted. In some embodiments, said aqueous sample is derived from a human, in some embodiments from a human body liquid. In an embodiment of the invention, the fluid sample is or is derived from human blood or blood plasma, urine, sputum, sweat, genital or buccal or nasal swabs, pipettable stool, or spinal fluid. In other embodiments, the fluid sample is human blood or blood plasma.

The "microfluidic chip" can be made of a variety of materials. For instance, suitable materials include, for instance, glass, plastics, quartz, silicon, or the like. In some embodiments, the material is a cyclic olefin polymer (COP) or copolymer (COC). Other suitable materials are known to the person skilled in the art. These materials also confer high optical transparency and a low level of autofluorescence, which is, for example, beneficial for optical detection as often used in nucleic acid analytics. In some embodiments, the entire microfluidic chip is made of the same material. In other embodiments, a non-transparent area, for example, towards the edges of the multiwell plate, may be made of a different material such as a more robust material for handling and protection purposes or the like. In some embodiments, the dimensions of the microfluidic chip are according to the ANSI/SLAS standards. These standards have been published by the Society for Laboratory Automation and Screening (SLAS) and can be found under "industry standards" at www.slas.org. In particular, the outside dimension of the base footprint is standardized as about 127.76 mm in length and 85.48 mm in width.

The term "reaction compartments", as used herein, represents sites in connection with the flow channel of the microfluidic chip described herein. The reaction compartments may comprise or be chambers or wells each having a sidewall, an upper end, and a closed lower end. Alternatively or additionally, the reaction compartments may comprise a hydrophilic pattern with a higher affinity to the aqueous sample than the walls of the flow channel, leading to a more efficient retention of the aqueous sample partitions in the reaction compartments. In some embodiments, the hydrophilic pattern may be induced by electrets or by external or internal electrodes to provide a charged surface having a higher surface energy and wettability than the walls of the flow channel. In the case of wells, the latter may be chemically inert on the inside, such that they do not interfere with the analytical reactions taking place within. In other embodiments, they may be coated with binding molecules such as biomolecules. Examples for biomolecules that may act, for instance, as capture molecules for binding either a target nucleic acid or other nucleic acids, include sequence-specific nucleic acid capture probes, such as DNA or LNA (Locked Nucleic Acid) probes. Another example would be streptavidin for interaction with a biotin tag at the target nucleic acid. Microfluidic chips described herein may have wells with diameters or wrench sizes—measured at the well opening which may, for example, be round, polygonal such as hexagonal, or the like—in the micro- to millimeter range, for example from 1 µm to 1 mm, or from 5 µm to 500 µm, or from 10 µm to 250 µm, or from 30 µm to 200 µm, or from 40 µm to 120 µm, or from 60 µm to 100 µm. In some embodiments, the wells have a diameter or wrench size of about 80 µm.

With regard to the volume of an individual well of microfluidic chips as described herein, a well may have a volume in the pico- to nanoliter range, such as from 1 pl to 100 nl, or from 5 pl to 50 nl, or from 10 pl to 1 nl, or from 50 pl to 500 pl, or from 75 pl to 250 pl. In some embodiments, the volume of a well is about 100 pl.

The number of wells in the optically transparent area of a multiwell plate as described herein may, for instance, be from 1000 to 1000000 wells, or from 5000 to 500000 wells, or from 10000 to 250000 wells, or from 20000 to 100000 wells. In some embodiments, the number of wells of a multiwell plate may be about 50000.

The reaction compartments are in fluid communication with the flow channel such that sample entering the flow channel can reach and be retained by the reaction compartments. The flow channel comprises a first material having a first affinity to the aqueous sample. The first material should be of such properties to allow the aqueous sample and the displacement fluid to enter the flow channel, whether by capillary action, pressure, or other force. The reaction compartments have a second affinity to the aqueous sample, and the second affinity is greater than the first affinity. The second affinity may be a property induced in the reaction compartments by chemical, optical, electronic, or electromagnetic means, for example. An exemplary chemical means to permanently induce an affinity may be, for example, an $O_2$ plasma exposure to a portion of a silicone surface to effectively change the affinity of the surface to retain an aqueous sample at the portion treated. Embedding ions in a surface may also be used to permanently induce an increased or decreased affinity at a location on a surface. An affinity may be temporarily induced according to some embodiments, for example, where a surface charge on a sample retaining or repelling surface is induced to increase the effective surface tension of that surface. In some embodiments of the method described herein, the difference of affinities enables the reaction compartments to collect a portion of sample from the flow channel and to retain the portion while the immiscible displacement fluid enters the flow channel via the inlet port, isolates sample retained by the reaction compartments, and displaces non-retained sample from the flow channel.

The displacement fluid is substantially immiscible with the aqueous sample as well as with the sealing agent. The displacement fluid may comprise resins, monomers, mineral oil, silicone oil, fluorinated oils, and other fluids which are substantially non-miscible with water or the sealing agent. According to some embodiments, the displacement fluid may be transparent, have a refractive index similar to glass, have low or no fluorescence, and/or have a low viscosity.

In some embodiments of the method described herein, the displacement fluid is an oil.

Both the sample to be isolated and the displacement fluid may be introduced into the flow channel by being drawn in under the influence of capillary forces. Pressurized loading techniques may also be used, but if displacement fluid is forced into the microfluidic chip under pressure, the pressure should not be so high as to displace sample from the reaction compartments. Other means of loading aqueous sample and/or displacement fluid may be used and include electrokinetic or electrostatic loading techniques, temperature differentials, centrifugal force, vacuum or suction loading, magnetic attraction loading of magnetic fluids, electrophoretic loading, or the like.

Among possible additional measures to facilitate gas exchange and pressure equilibration is the active application of pressure on the microfluidic chip from the outside.

Consequently, in some embodiments of the method described herein, the series of heating steps takes place within a pressurized chamber.

In this regard, it may be advantageous to maintain an increased pressure within said chamber in relation to ambient pressure. The pressure within the pressurized chamber may be between 1 and 10 bar, or between 1 and 5 bar, or between 1 and 2 bar. In some embodiments, the pressure is about 1.5 bar.

The relative overpressure so exerted on the liquids within the microfluidic chip by gas exchange and pressure equilibration through the inlet port, enabled by the molten sealing agent, reduces the risk of bubble formation, as it contributes to preventing any gas inclusions within the flow channel and/or reaction compartments from expanding.

In further embodiments, the method described herein can be further streamlined and facilitated by pre-loading the sealing agent into the inlet port. Advantageously, the sealing agent may be attached to an inner wall of the inlet port, leaving a gap sufficiently wide so as to not obstruct liquid passage through the inlet port while the sealing agent is in solid state. The so prepared microfluidic chip can then be transported, for example, from its production site to the laboratory in which it is used. In contrast to microfluidic chips that, for instance, are sold and distributed with a solid mechanical plug sealing the inlet port, the currently described sealing agent does not have to be removed prior to filling the aqueous sample into the microfluidic chip in its destination laboratory and then re-applied to the inlet port ("de-capping/re-capping"), but is molten into place once the chip has been properly loaded with sample and displacement fluid. Further in contrast to a traditional plug, the currently described sealing agent is fully compatible with the pressure phenomena during thermal incubation as described above.

Hence, in some embodiments of the method described herein, the microfluidic chip in step a. is preloaded with the sealing agent which is attached to an inner wall of the inlet port in solid state so as to not obstruct the passage of the aqueous sample or the displacement fluid through the inlet port into the flow channel.

The use of a sealing agent, especially, while not only, in the currently described embodiment where the inlet port is pre-loaded with it, further has the advantage that no separate parts such as plugs need to be produced, distributed and ultimately handled together with the microfluidic chip. For instance, removing a pre-applied plug prior to filling the microfluidic chip and then placing it back on- or into the inlet port typically confers an increased risk of cross contamination, especially in methods were this is performed manually. For instance, a plug may be inadvertently touched or dropped by, for example, clinical personnel. Furthermore, a traditional plug is a separate part of a microfluidic chip and therefore has to be produced separately, which may also increase the cost of a respective microfluidic chip. Financial considerations are of particular significance in embodiments where the microfluidic chip is disposable and should be as inexpensive as possible.

"Disposable", in the context used herein, relates to a device or product that is used only a few times, in some embodiments only once, before it is discarded. Nucleic acid analysis involving amplification, such as PCR, is generally more sensitive to contamination than other techniques, as minute amounts of contaminating agents such as undesired nucleic acid sequences may be inadvertently amplified. In this context, disposable microfluidic chips reduce the risk of carryover contamination between experiments.

In some embodiments of the method described herein, the sealing agent in solid state is held by an injection channel formed as a groove or protrusion of an inner wall of the inlet port, wherein the injection channel and the inlet port are fluidically connected. The injection channel may be open at the lower or at both ends, thus fluidically connecting the channel to the inlet port. In other words, once the sealing agent is molten, it may flow through one of the channel openings into the inlet port, create a liquid layer upon the displacement fluid, and re-solidify by lowering the temperature below the sealing agent's melting point.

Similar embodiments may be useful to the person skilled in the art, for example, where the inlet port has a cylindrical or conical shape and the sealing agent is pre-applied to the inner circular wall of the inlet port in the form of a solid ring. In such embodiments, the application of the sealing agent upon melting may be particularly homogeneous, as it is surrounds the opening of the inlet port and may flow down onto the surface of the displacement fluid from its outer limits along its entire circumference.

It may be advantageous in the context described herein if the microfluidic chip has more than one port. In particular, the microfluidic chip in some embodiments further comprises an outlet port. The latter may advantageously be located at the opposite end of the flow channel from the inlet port. Hence, the inlet port and the outlet port may be in fluid communication through the flow channel. In some embodiments, the aqueous sample is introduced into the flow channel through then inlet port, fills the reaction compartments in fluidic connection with the flow channel, while excess aqueous sample exits the flow channel through the outlet port, or air displaced by the aqueous sample from the flow channel can leave the flow channel through the outlet port, in which case the outlet port serves as an exit vent preventing pressure increases caused by trapped air. In embodiments where the microfluidic chip also has an outlet port, the latter is treated or pre-loaded equally as the inlet port. In other words, the sealing agent in step d. is also applied to the outlet port such that inlet port and outlet port are both sealed with the solidifying sealing agent. In embodiments where the inlet port is pre-loaded with sealing agent in solid state, the outlet port is likewise pre-loaded with sealing agent in solid state, in some embodiments in exactly the same fashion.

The advantages described earlier in connection with the inlet port and the sealing agent with a melting temperature above room temperature also apply to the outlet port if present. For instance, during thermocycling, the sealing agent is molten in both the inlet and the outlet port during at least one step, both ports consequently providing for gas exchange and pressure equilibration.

In some embodiments of the method described herein, the aqueous sample, the displacement fluid and the sealing agent are filled into the flow channel in a filling station, while the series of heating steps is applied in a thermal incubation station spatially separated from the filling station.

In such embodiments, the spill protection conferred by the solidified sealing agent plays an especially crucial role during the transport from the filling station to the thermal incubation station. It often makes sense to spatially separate the thermal incubation station from other analytical modules such as the filling station, as particularly methods such as PCR are prone to contamination by undesired nucleic acids which may even be distributed via aerosols.

A "filling station", as used herein, comprises elements required for dispensing the aqueous sample, the displacement fluid, and the sealing agent in molten form into the microfluidic chip. Such elements may comprise pipettes with or without disposable pipette tips. Pipettes may also be needles made of steel or similar suitable materials. Also in some embodiments, the filling station comprises a heating element suitable for melting the sealing agent. For instance, a pipetting needle may be heatable so as to melt sealing agent in solid state upon contact, aspirating it into the hollow inside of the needle, and dispensing it into the inlet port or into the inlet and outlet port. In further embodiments, the filling station may comprise means to apply pressure, such as pumps or the like.

The term "thermal incubation station", as used herein, represents an instrument or module comprising heating and, in some embodiments, also cooling elements. Such elements comprise, for instance, Peltier elements. In some embodiments, the thermal incubation station is a thermocycler such as a PCR cycler on which pre-defined temperature profiles are programmable to conduct cycles of coordinated heating steps or heating and cooling steps. In some embodiments, no active cooling is involved. In further embodiments, the thermal incubation station may comprise a pressurized chamber with the advantages described herein.

In some embodiments of the method described herein, the series of heating steps drives a polymerase chain reaction within the reaction compartments containing the partitions of the aqueous sample.

As used herein, the term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Generally, a PCR cycle comprises a denaturation step at usually above 90° C. in which the individual strands of a double-stranded template nucleic acid are separated from each other. At a significantly lower temperature, often between 50° C. and 65° C., the primers anneal to their complementary target sites on the respective templates strands, before the temperature is ramped up again to mostly between 70° C. to 80° C., where the thermostable nucleic acid polymerase exhibits its maximum enzyme activity. Methods for a great variety of PCR applications are widely known in the art, and described in many sources, for example, Ausubel et al. (eds.), Current Protocols in Molecular Biology, Section 15, John Wiley & Sons, Inc., New York (1994).

In such embodiments, the melting temperature of the sealing agent is, for instance, exceeded at least during the denaturing step of a cycle, typically occurring at above 90° C., for example, at about 94° C.

Another aspect described herein is a microfluidic chip for thermally incubating an aqueous sample suspected to contain a target nucleic acid, the microfluidic chip comprising:
 a flow channel between an upper plate and a lower plate,
  the flow channel being in fluid connection with a plurality of reaction compartments on the inside wall of the upper plate and/or the lower plate;

an inlet port in fluid communication with the flow channel;

a sealing agent having a melting point above room temperature attached to an inner wall of the inlet port in solid state so as to not obstruct the passage of the aqueous sample, wherein the sealing agent is immiscible with and has a lower density than the aqueous sample.

Such a microfluidic chip confers the advantages recited in the context of the method described herein in embodiments where the inlet port is pre-loaded with the sealing agent in solid state.

In some embodiments of the microfluidic chip described herein, the sealing agent is held by an injection channel formed as a groove or protrusion of an inner wall of the inlet port, wherein the injection channel and the inlet port are fluidically connected, as set out in the context of the method described herein.

Also in some embodiments of the microfluidic chip described herein, the sealing agent spans the inner circumference of the inlet port so as to surround the opening within the inlet port. This can lead to a particularly homogeneous distribution of the molten sealing agent onto the surface of the displacement fluid, as detailed in the context of the method described herein.

In further embodiments, the microfluidic chip described herein further comprises an outlet port in fluid communication with the flow channel, wherein the sealing agent is further attached to an inner wall of the outlet port in solid state so as to not obstruct the passage of the aqueous sample.

The advantages of such embodiments are consistent with the advantages of the embodiments involving an outlet port of the method described herein.

Since it is often advantageous to acquire and use integrated solutions for analytics or diagnostics, another aspect described herein is a kit for thermally incubating an aqueous sample suspected to contain a target nucleic acid, the kit comprising:

the microfluidic chip described herein;

a displacement fluid immiscible with both the aqueous sample and the sealing agent.

In some embodiments, the order of density from high to low is aqueous sample>displacement fluid>sealing agent.

The specifications of the displacement fluid and the sealing agent are as in the context of the method described herein.

Such a kit may comprise further components, as known by the skilled person. For instance, the kit may comprise reagents useful in the thermal incubation reaction as described herein.

The kit described herein may itself form part of an analytical system for thermally incubating an aqueous sample suspected to contain a target nucleic acid, the analytical system comprising:

the kit described herein;

a filling station configured to fill the aqueous sample, the displacement fluid and the sealing agent in liquid state into the flow channel of the microfluidic chip;

a thermal incubation station configured to subject the microfluidic chip to a series of heating steps, wherein in one or more steps the melting temperature of the sealing agent is exceeded such that it is molten, thereby allowing for the exchange of gas and pressure equilibration through the inlet port.

The schematic drawing of FIG. 1 depicts an embodiment of the microfluidic chip (1) described herein in a perspective view from above. The upper plate (3) of this embodiment is made of a transparent material, such that the flow channel (2) is visible. A transparent upper plate (3) has various advantages, for instance, the optical detection of analytes within the reaction compartments (5) from above may be enabled. In embodiments where also the lower plate (4) is transparent, optical detection based on light transmission is also possible. The reaction compartments (5), in this embodiment hexagonally shaped wells formed as cavities in the upper surface of the lower plate (4), can be filled with aqueous sample (10) through the inlet port (6) being in fluid communication with the flow channel (2). The outlet port (7) provides an exit vent for displaced air or even an exit opening for excess aqueous sample (10) or displacement fluid (20). Both ports in this embodiment display a cylindrical shape and are formed as upward protrusions of the upper plate (3). Other suitable port geometries are possible.

The microfluidic chip (1) depicted in this embodiment has a linear flow channel (2) stretching between the inlet port (6) and the outlet port (7). Other geometries of the flow channel (2) are conceivable. For instance, the flow channel (2) may be curved. According to the method described herein, the sealing agent (30) is applied to both the inlet (6) and the outlet port (7) so as to seal all openings of the flow channel (2), thereby protecting the aqueous sample within the microfluidic chip (1) from spilling and contamination. The aqueous sample (10), the displacement fluid (20) and the sealing agent (30) are not depicted in this figure for the sake of clarity.

Figure 2:
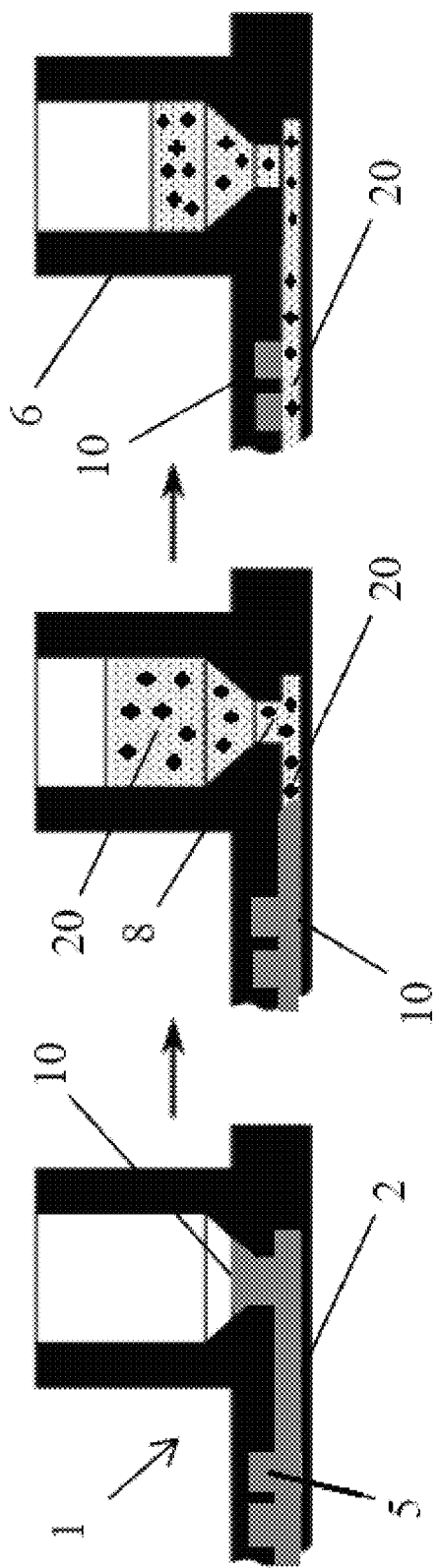
FIGS. 2A-2C schematically depict the filling procedure of the microfluidic chip (1) described herein with regard to aqueous sample and displacement fluid in a cross-sectional side view.

A sequence of the filling procedure of the microfluidic chip (1) is schematically depicted in the cross-sectional side view of FIG. 2. Each of the three drawings shows the cross-section of the inlet port (6) and a part of the flow channel (2) with the reaction compartments (5). The image on the left-hand side shows the aqueous sample (10) having been filled into the reaction compartments (5) and the flow channel (2) through the inlet port (6). The latter has a cylindrical main body and assumes a tapered shape towards its fluid connection with the flow channel (2), such that the inlet port (6) can hold a reasonable volume of liquid within its main body while a relatively slow and controlled passage of the respective liquid into the flow channel (2) is provided by the narrow fluidic interface (8) between inlet port (6) and flow channel (2).

The reaction compartments (5) in this embodiment are wells formed in the upper plate (3) rather than the lower plate (4), such that their openings face downwards into the flow channel (2). The aqueous sample (10) is drawn into the wells (5) by capillary action and/or under the application of pressure through the inlet port (6).

The image in the middle represents the step in which the displacement fluid (20) is dispensed into the inlet port (6) to displace the aqueous sample (10) from the flow channel (2) without displacing the aqueous sample (10) partitions from the reaction compartments (5). Their mutual immiscibility prevents the aqueous sample (10) and the displacement fluid (20) from uniting to a mixture. The current depiction shows a transient state in which the displacement fluid (20) has already partly displaced the aqueous sample (10) from the flow channel (2).

The third image on the right-hand side of FIG. 2 shows a subsequent state of the process in which the displacement fluid (20) has fully displaced the aqueous sample (10) from the flow channel (2) and thereby entrapped the partitions of the aqueous sample (10) within the individual reaction compartments (5).

Figure 3:
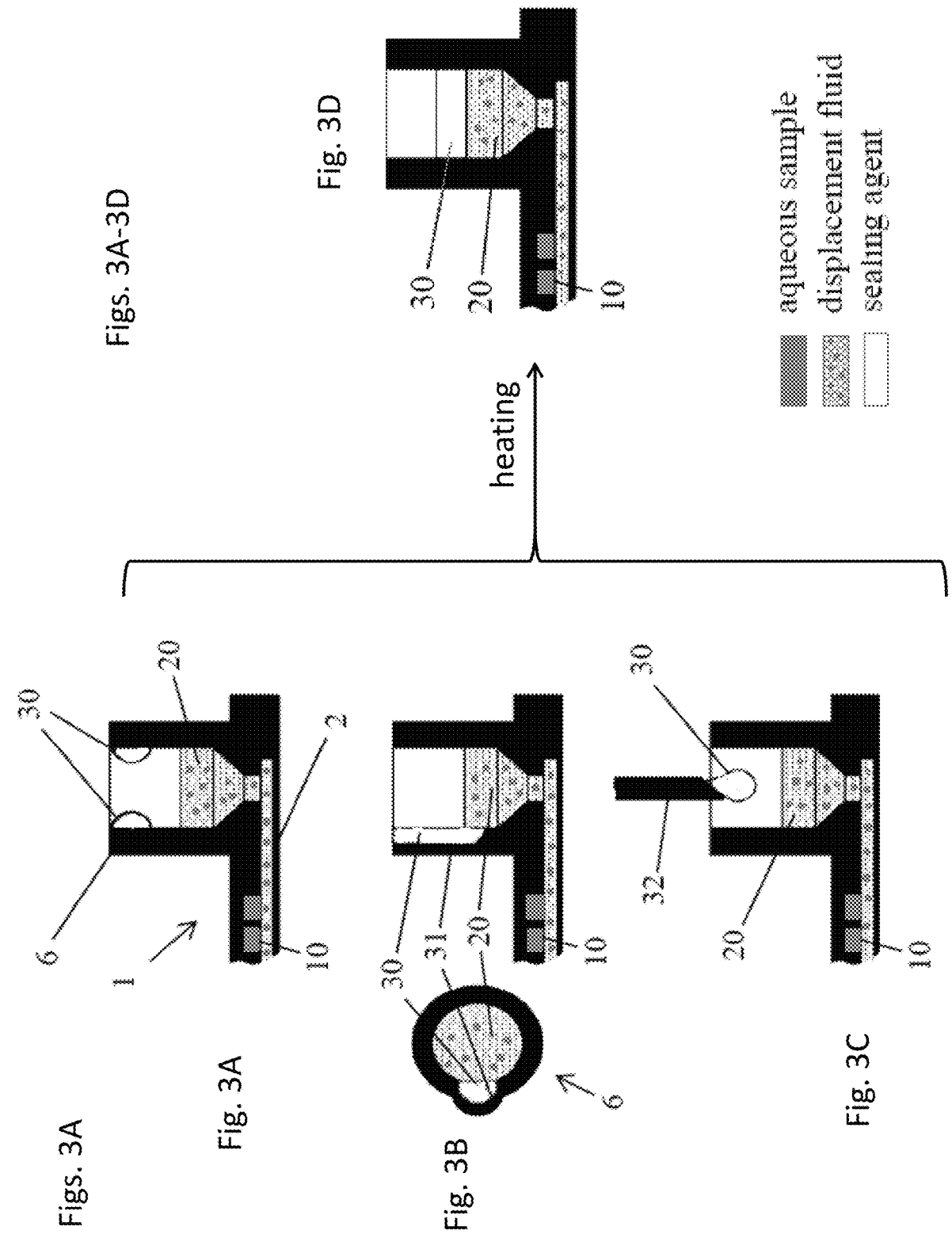
FIGS. 3A-3D features a schematic cross-sectional side view of three different embodiments of the application of sealing agent within the inlet port (6).

The drawing of FIG. 3 shows different embodiments of the sealing of so prepared microfluidic chips (1) with sealing agent (30).

Variant a) (FIG. 3A) displays an inlet port (6) having two portions of sealing agent (30) in solid state attached to its inner wall to the left and to the right, leaving a gap in between so as to not obstruct fluid passage of aqueous sample (10) or displacement fluid (20). As this drawing features a cross-sectional side view, the sealing agent (30) may also form a continuous ring along the inner wall of the inlet port (6).

Variant b) (FIG. 3B) represents an embodiment in which the sealing agent (30) in solid state is held by a reservoir in the shape of a groove (31) formed by an elongate semi-circular depression of a portion of the inner wall of the inlet port (6), as can be seen in more detail on the left-hand side showing a cross-sectional top view of the inlet port (6).

Variant c) (FIG. 3C) exemplifies an embodiment of the method described herein, wherein the inlet port (6) is not pre-loaded with sealing agent (30) in solid state, but the latter is dispensed into the inlet port (6) in molten form by a pipetting needle (32).

The arrow indicates a heating process to a temperature above the melting temperature of the sealing agent (30), such that the latter is molten and may flow into place to form an immiscible layer upon the surface of the displacement fluid (20) within the inlet port (6) as shown in FIG. 3D. In this stage, the sealing agent (30) is allowed to re-solidify upon lowering the temperature either actively by cooling or passively by incubation at room temperature. The microfluidic chip (1) with partitioned aqueous sample (10) in its reaction compartments (5) is now sealed and suitably prepared for handling, transportation, or the like. For instance, it may be transported from a filling station to a thermal incubation station.

Figure 4:
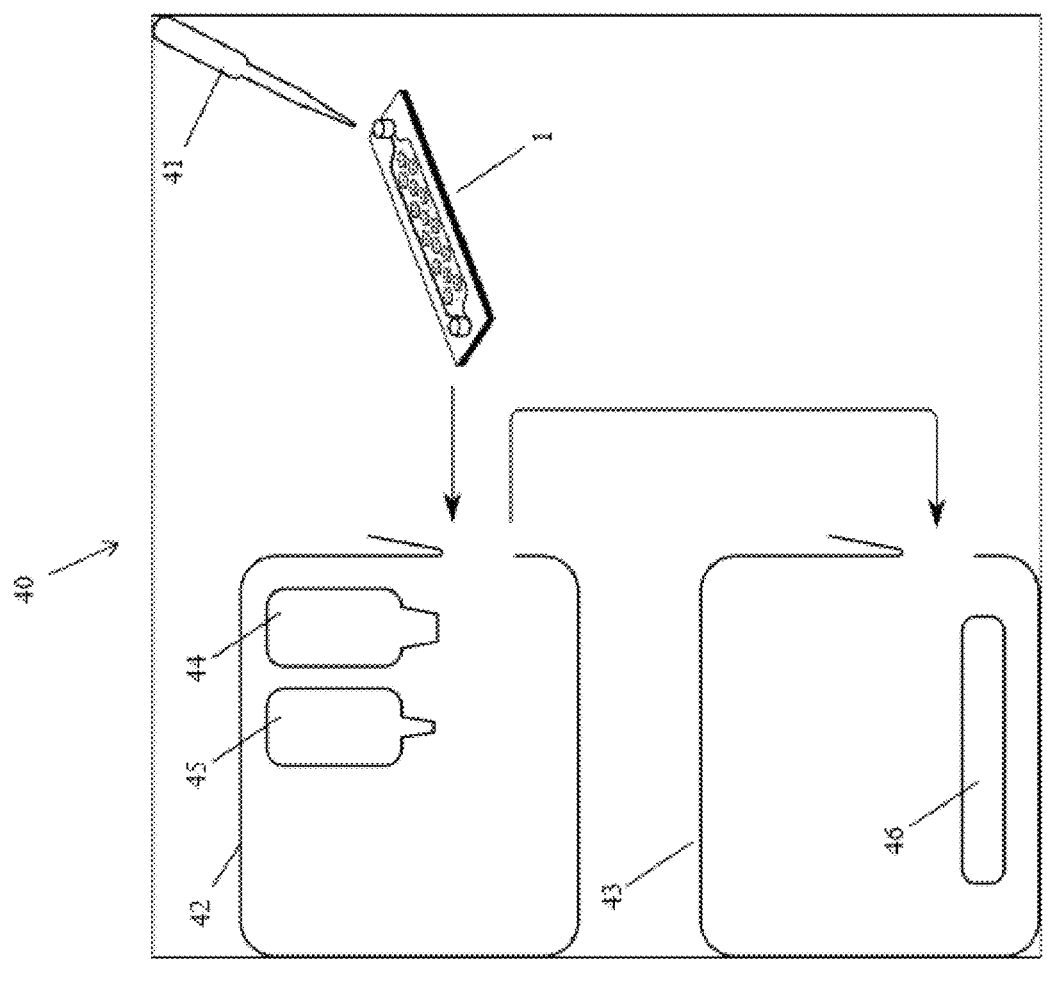
FIG. 4 provides a schematic drawing of the analytical system (40) described herein.

The scheme shown in FIG. 4 depicts the typical workflow of an embodiment of the analytical system (40) described herein. The microfluidic chip (1) is first filled with the aqueous sample (10) in a first location comprising the filling station (42). In the depicted embodiment, the aqueous sample (10) is applied manually by means of a pipettor (41). Other suitable dispensing means for the aqueous sample (10) are also possible. The presented embodiment further features an automated dispenser (44) for the displacement fluid (20) as well as an automated dispenser (45) for the sealing agent (30). In some embodiments, the dispenser (45) may alternatively or additionally comprise or be a heating element. Once the microfluidic chip (1) has been prepared by application of aqueous sample (10), displacement fluid (20), and sealing agent (30), and the sealing agent (30) has or has been re-solidified to seal the microfluidic chip (1), the latter is transported (lower arrow) to the thermal incubation station (43) comprising a heating element (46) such as a Peltier element or the like. In the thermal incubation station (43), a reaction such as a PCR may take place, during which the sealing agent (30) is temporarily molten and thus provides for gas exchange and pressure equilibration.

EXAMPLES

The following examples are intended to illustrate certain embodiments in which the disclosure can be worked.

Example 1: Suitability of Paraffin Wax as Port Sealing Agent for Spilling Protection Objective: Inlet port sealing with sealing agent shall serve as spilling protection if the chip is accidentally turned over or drops to the floor.

Materials: (1) Microfluidic chip with inlet and outlet port suitable for receiving a volume of 45 µl of separation fluid and 45 µl of sealing agent. The microfluidic chip features a flow channel with a total volume of 10 µl and a plurality of compartments inside the flow chamber that comprise a total volume of 10 µl; (2) Generic PCR Mastermix: ROCHE LightCycler® Multiplex DNA Master, 07339585001 (Roche Diagnostics Corporation, Indianapolis, IN 46250-0414 USA); (3) Sealing agent: paraffin wax. Fisher Chemical, UK, CAS: 8002-74-2, EC: 232-315-6, clearing point about 55-71° C.; (4) Displacement fluid: Silicone fluid Xiameter PMX-200, 50 CS, Credimex AG, Alpnach, Switzerland; and (5) Heating plate and vessel to melt 20 g of paraffin wax.

A microfluidic chip was filled with 10 µl (equals the sum of the volumes of the compartments within the chip) of PCR reaction mix (1 part 5×Mastermix and 4 parts water). The microfluidic chip was filled with displacement fluid by pipetting displacement fluid into the chip with gentle pressure, using a pipette tip making pressure tight contact to the inlet port. A volume of 110 µl was used, so that the flow channel of the microfluidic chip was filled, and the inlet and outlet port of the chip were filled approximately half (45 µl). Paraffin wax was melted in a vessel (aluminum foil) on the heating plate at 60° C. A pipette tip with large opening was used to pipette the wax. A volume of 45 µl was gently aspirated into the pipette tip, thereby letting the pipette tip acclimate to the temperature of the molten wax. The melted paraffin wax was pipetted into the inlet and outlet port of the microfluidic chip. The time was measured until the solidifying process was finished. Spillage (drop-test) protection was tested 1 minute after application of paraffin wax. The chip was dropped to the floor from a height of 1.5 m and potential flow out or spillage of any liquid after impact on ground was observed. Spillage (flow-out) protection was tested after drop-test by turning the microfluidic chip upside down and observing flow out of any liquid for a time period of 3 minute.

The experiment was conducted using paraffin wax as a sealing agent and silicone fluid PMX 200 as displacement fluid. A number of 24 chips were processed. The wax curing was sufficient after 1 minute of waiting time at room temperature. The drop-test was passed by all investigated chips, i.e. no spillage or flow out of liquid was observed.

Example 2: Low Autofluorescence of Paraffin Wax as Port Sealing Agent

Objective: Autofluorescence is an unwanted material property within a microfluidic setup that includes a biomolecular assay that is based on fluorescence readout. The contribution to total fluorescent signals has to be assessed for all materials within the imaging area. Even though the inlet and outlet port are not in primary focus of imaging on the microfluidic chip, scattered light might interact with the sealing agent and result in an unwanted signal.

Materials: (1) Microfluidic chip and paraffin wax as described in Example 1; (2) PCR Mastermix from Example 1 containing 1 micromolar FAM (6-Carboxyfluorescein) dye solution; (3) Imaging device suited for fluorescence imaging of the microfluidic chip containing the fluorescence buffer solution, such as an epifluorescence microscope with an appropriate filter set.

The microfluidic chip was filled with the PCR reaction solution containing fluorescence dye as described in Example 1. A drop of paraffin wax was applied onto the top of the reaction compartment area (i.e. imaging area) of the microfluidic chip. The thickness of the drop was adjusted to approximately 2 mm. The microfluidic chip containing the fluorescent solution inside the reaction compartments and the wax layer covering a part of the top of the chip was subjected to fluorescence imaging. The fluorescence intensity on the image of the chip was measured in the compartment area and also on the area covered by paraffin wax.

The fluorescence (after background subtraction) measured inside the compartments accounted for 31250±3562 RFU (relative fluorescence units). The fluorescence from the paraffin wax spot in the imaging area accounted for 10875±740 RFU. The fluorescence signal emitted by the paraffin wax spot made 35 percent of the signal of interest only. As this experiment describes an extreme case, since the thickness of the spot was chosen very large, and in the target application, the paraffin wax is outside the imaging area, the autofluorescence level detected is negligible for the target application.

Example 3: Digital PCR Performance in a Microfluidic Chip with Paraffin Wax-Sealed Inlet and Outlet Objective: Comparison of performance of a digital PCR experiment in a microfluidic chip with and without inlet and outlet port sealing: a biochemical quantification assay such as digital PCR shall not be negatively influenced in performance by using paraffin wax as sealing agent.

Materials: (1) The microfluidic chip, displacement and sealing fluid, and generic PCR Mastermix described in Example 1; (2) A generic internal control: PCR primer and probe set on FAM and HEX channel, and a nucleic acid target of known concentration to conduct a PCR and compare the result; (3) A thermal cycler and imager instrument to conduct PCR with the microfluidic chip and measure fluorescence signal after thermal cycling inside the compartments in the microfluidic chip. The thermal cycler instrument is able to thermally cycle a microfluidic chip between room temperature and 98° C. Furthermore the instrument is able to conduct the cycling in a pressurized setting of plus 1.5 bar.

The PCR reaction mix was prepared from Mastermix, primer/probe set and target as described in the Mastermix kit manual. A total number of three experiments were conducted with wax as sealing agent, and a total number of three experiments were conducted as control without inlet and outlet port sealing. The PCR reaction mix (10 µl) was pipetted into the microfluidic chip per experiment. The displacement fluid (110 µl) was pipetted into the flow channel by gentle pressure. The paraffin wax was applied into the inlet and outlet port (45 µl each) as described in Example 1. In the control experiments, no sealing agent was added. The microfluidic chip was subjected to the thermal cycling instrument. The microfluidic chip was set under a pressure of plus 1.5 bar and subsequently subjected to a thermal cycling: preincubation at 95° C. for 2 minutes and 40 cycles of: 10 seconds at 95° C. and 20 seconds at 58° C. Final cool down to 40° C. for 30 seconds. Thermal heating and cooling ramps: 1.2° C. per second. The lid of the thermal cycler was held at a constant temperature of 58° C. Fluorescence intensity of each compartment in the FAM and HEX channel was read out in the fluorescence reader instrument. The fluorescence values were used for the determination of the number of positive PCR reactions in the compartments, applying a fixed threshold, and subsequent calculation of the initial number of target molecules (copy number) using Poisson statistics. The quantification result of the microfluidic chip sealed with paraffin wax was compared to the non-sealed control chip. Also the fluorescence intensities of the positive and the negative compartments were compared between sealed and non-sealed control chip. The state of the inlet an outlet port wax sealing after thermal cycling was optically compared to the state before cycling.

For the control experiment, the copy number per µl determined in the FAM channel accounted to 1239±30, and for the HEX channel to 6246±299. For the experiment with paraffin wax as sealing agent, the determined copy number per µl in the FAM channel accounted to 1188±72, and for the HEX channel to 6213±210. The difference in copy number counts between the paraffin wax sealed microfluidic chips and the control experiments are not statistically significantly different (unpaired t-test, P=0.3207 for FAM, and P=0.8833 for HEX). Also the mean fluorescence intensities [RFU] of the three sealed and non-sealed experiments are statistically not significantly different, both for positive and negative signals. Welch's t-Test for FAM[positive signals]: w/o wax: 4885±12 versus w/wax: 4883±29: P=0.9215. FAM[negative signals]: w/o wax: 760±2 versus w/wax: 749±4: P=0.0554. HEX[positive signals]: w/o wax: 11411±30 versus w/wax 11333±42: P=0.2140. HEX[negative signals]: w/o wax: 2465±11 versus 2448±39: P=0.5414. The visual observation of the microfluidic chips after cycling showed that the inlet and outlet port seals were still intact, with a minimal amount of separation fluid found on top of the seal, which is considered non-critical.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A microfluidic chip for thermally incubating an aqueous sample comprising target nucleic acid, the microfluidic chip comprising, from a proximate to a distal end:
   an inlet port for receiving the aqueous sample, the inlet port comprising an inner wall including a sealing agent attached to the inner wall of the inlet port in a pre-loaded solid state so as to not obstruct the passage of the aqueous sample through the inlet port while the sealing agent is in the pre-loaded solid state, said sealing agent having a melting point above room temperature and being immiscible with and having a lower density than the aqueous sample, wherein the sealing agent is a wax; and
   a flow channel positioned between an upper plate and a lower plate of the microfluidic chip, the flow channel being in fluid communication with the inlet port and a plurality of fixed reaction compartments positioned on one or more surfaces of an inside wall of the upper plate and the lower plate, the reaction compartments comprising a plurality of fixed wells, wherein each of the fixed wells comprises a sidewall, an upper end, and a closed lower end;

wherein the sealing agent is configured to displace from the pre-loaded solid state and solidify so as to seal the inner wall of the inlet port once the aqueous sample has been displaced from the inlet port through the flow channel and separated into one or more of the plurality of fixed wells.

2. The microfluidic chip of claim 1, wherein the inlet port further comprises an injection channel positioned in the inner wall of the inlet port, the injection channel including at least one or more elements selected from a groove and protrusion, and the sealing agent is positioned in the injection channel in the pre-loaded solid state, wherein the injection channel and the inlet port are fluidically connected.

3. The microfluidic chip of claim 1, wherein the inlet port comprises an opening and the sealing agent spans an inner circumference of the inlet port in the pre-loaded solid state, thereby surrounding the opening within the inlet port.

4. The microfluidic chip of claim 1, further comprising an outlet port distal from the inlet port and in fluid communication with the flow channel, wherein the sealing agent is further attached to an inner wall of the outlet port in an additional pre-loaded solid state.

5. A kit for thermally incubating an aqueous sample suspected to contain a target nucleic acid, the kit comprising the microfluidic chip of claim 1; and a displacement fluid immiscible with both the aqueous sample and the sealing agent.

6. An analytical system for thermally incubating an aqueous sample comprising a target nucleic acid, the analytical system comprising:
the kit of claim 5;
a filling station configured to fill the aqueous sample, the displacement fluid and the sealing agent in a liquid state into the flow channel of the microfluidic chip;
a thermal incubation station configured to subject the microfluidic chip to a series of heating steps, wherein in one or more of the heating steps the melting temperature of the sealing agent is exceeded such that it is molten, thereby allowing for the exchange of gas and pressure equilibration through the inlet port.

7. The microfluidic chip of claim 1, wherein the sealing agent is configured to allow for exchange of gas and pressure equilibration through the inlet port when the melting temperature of the sealing agent is exceeded such that it is molten.

* * * * *